United States Patent [19]

Borsanyi

[11] Patent Number: 5,053,031
[45] Date of Patent: Oct. 1, 1991

[54] PUMP INFUSION SYSTEM

[75] Inventor: Alexander S. Borsanyi, Newport Beach, Calif.

[73] Assignee: Baxter International Inc., Deerfield, Ill.

[21] Appl. No.: 324,589

[22] Filed: Mar. 21, 1989

Related U.S. Application Data

[63] Continuation-in-part of Ser. No. 174,590, Mar. 29, 1988.

[51] Int. Cl.$^5$ .............................................. A61M 9/22
[52] U.S. Cl. ................................ 604/891.1; 604/132; 604/153; 128/DIG. 12
[58] Field of Search ............... 604/9, 10, 93, 131, 604/132, 175, 185, 891.1, 151, 153; 128/DIG. 12

[56]  References Cited

U.S. PATENT DOCUMENTS

| | | | |
|---|---|---|---|
| 3,468,308 | 9/1969 | Bierman | 604/132 X |
| 4,193,397 | 3/1980 | Tucker et al. | 604/131 X |
| 4,265,241 | 5/1981 | Portner et al. | 604/131 |
| 4,386,929 | 6/1983 | Peery et al. | 604/132 |
| 4,419,096 | 12/1983 | Leeper et al. | 604/132 |
| 4,525,165 | 6/1985 | Fischell | 604/131 |
| 4,699,615 | 10/1987 | Fischell et al. | 604/131 |
| 4,741,733 | 5/1988 | Winchell et al. | 604/51 |
| 4,772,263 | 9/1988 | Dorman et al. | 604/132 |
| 4,781,688 | 11/1988 | Thoma et al. | 604/132 |
| 4,813,951 | 3/1989 | Cannon | 604/891.1 |
| 4,838,887 | 6/1989 | Idriss | 604/891.1 |
| 4,857,059 | 8/1989 | Rey et al. | 604/185 |
| 4,898,585 | 2/1990 | Borsanyi et al. | 604/153 |
| 4,938,751 | 7/1990 | Leeper et al. | 604/132 |

Primary Examiner—John D. Yasko
Assistant Examiner—Adam J. Cermak
Attorney, Agent, or Firm—Sandra S. Schultz; June M. Bostich; Michael C. Schiffer

[57]  ABSTRACT

An infusion system includes an implantable housing having a storage reservoir that is dimensioned and arranged to contain a supply of a medication and a holding reservoir that is dimensioned and arranged to receive a dosage of the medication from the storage reservoir. A pump assembly is included for enabling a patient to cause a dosage of the medication to be transferred from the storage reservoir to the holding reservoir, and pressurizing components maintain the dosage under pressure within the holding reservoir in order to cause the dosage to discharge through an output port to the infusion location. One embodiment accomplishes this with an elongated bladder of elastomeric material in fluid communication with the storage reservoir and the output port. The bladder inflates as it fills with the dosage to maintain the dosage under pressure, and a capillary element disposed intermediate the bladder and the output port restricts the rate of discharge. This embodiment allows the dispensing of medication at a uniform constant flow rate.

7 Claims, 3 Drawing Sheets

PUMP INFUSION SYSTEM

This application is a continuation-in-part of U.S. Pat. application Ser. No. 07/174,590, filed Mar. 29, 1988.

BACKGROUND OF THE INVENTION

1. Technical Field

This invention relates generally to infusion systems for the administration of medications, and more particularly to a new and improved infusion system that is subcutaneously implantable.

2. Background Information

An implantable infusion system generally includes a reservoir within a housing having a size, shape, and biocompatible exterior suitable for subcutaneous positioning within a patient's body. Medications to be administered are periodically injected into the reservoir using a syringe by inserting the needle through a self-sealing dome on the housing, and a catheter is positioned to direct the medications from the reservoir to a selected portion of the patient's body. A pump and valving arrangement transfers the medications from the reservoir to the catheter under patient control, and this allows the patient to administer required medications in precise quantities while minimizing the number of injections required and the number of visits made with a physician.

However, many existing infusion systems have certain problems that need to be overcome. For example, the pump may be actuated by the patient depressing an actuator or plunger on the housing in a desired number of strokes, each stroke transferring a known dosage. As the actuator is stroked, the dosage passes through the catheter to the infusion location. Thus, the total dosage is administered substantially all at once.

Although this suffices in many cases, it is sometimes preferred that the dosage be administered more slowly at a substantially constant flow rate, a little at a time over a relatively prolonged period. In order to do this with existing infusion systems, the dosage per stroke must be kept small and the actuator must be stroked again and again during the entire period of administration. Thus, the patient must expend more time and effort than preferred while remaining relatively attentive to the administration procedure. Even under these conditions, a continuous flow cannot be secured because of the instantaneous discharge of the small doses. Consequently, it is desirable to have a new and improved infusion system that overcomes these concerns--one capable of administering the dosage more slowly with less patient involvement at a more continuous flow rate.

Another problem with various existing infusion systems is their inability to store multiple dose quantities at one time. Also, many are electrical in operation, requiring batteries or the like, and running the risk of a sudden, unexpected loss of power.

Finally, the existing systems that do solve some of these problems require surgical implantation of more than one part, each part usually in a separate incision resulting in extensive tissue damage. The parts are connected together during surgery, thereby increasing the difficulty of the implantation procedure and the cost and risk to the patient.

SUMMARY OF THE INVENTION

This invention recognizes the problems associated with the prior art and provides a new and improved infusion system with the desired attributes.

Briefly, the above and further objects of the present invention are realized by an implantable infusion system that provides a substantially continuous, constant flow rate, generally over a substantial period of time and at least for a given dose. This is accomplished with a first or storage reservoir for storing the medications, and a second or holding reservoir into which the dosage is pumped and maintained under substantially constant pressure.

Thus, a substantially continuous, constant flow rate is achieved to overcome many problems of the prior art. The dosage is administered a little at a time over a prolonged period, that is at such a continuous, constant flow rate that the total volume of the dose delivered to the patient is equal to the amount the patient dispensed by activating the pump. The patient need only stroke the actuator to charge the holding reservoir. Delivery then proceeds slowly, without further patient involvement.

Generally, an infusion system constructed according to the invention includes an implantable housing in which to store a medication. The housing may be similar in some respects to implantable devices of existing infusion systems, employing a biocompatible exterior suitable for subcutaneous implantation within the body of a patient, and a self-sealing dome through which the medication is injected. However, in another major aspect of the invention, the entire device of the present invention is enclosed in one housing, to minimize the number of surgical incisions required for implantation and to largely eliminating interconnecting the elements of the device during surgical implantation.

According to a major aspect of the invention, the housing includes both a storage reservoir that is dimensioned and arranged to contain a supply of a medication and a holding reservoir that is dimensioned and arranged to receive a dosage of the medication from the storage reservoir. The transferred dosages are multiples of the stroke volume of the delivery pump. A typical stroke volume is between one-tenth and two-tenths cubic centimeters. The holding reservoir is therefore capable of accommodating relatively large doses of drugs.

The holding reservoir is designed to maintain or generate a substantially constant pressure level independently from the volume of the drug in the holding reservoir. This is accomplished by utilizing an elastomeric wall (usually configured in a certain fashion) or a flexible wall compressed by a constant rate spring.

A dosage of a medication that has been injected into the storage reservoir is transferred to the holding reservoir by the patient operating a pump and valving arrangement within the housing. A plunger-like actuator that the patient strokes may be used for this purpose, each stroke transferring a known quantity of the medication to the holding reservoir where it is maintained under pressure for discharge through an output port and a catheter to an infusion location within the body of the patient, slowly and over a substantial period of time. After one dose has been fully delivered. the patient activates the device again to deliver another dose, thus achieving in essence complete continuity of dose delivery over time.

According to another aspect of the invention, a specialized pressurizing arrangement maintains the dosage under pressure in the holding reservoir. An elastomeric bladder disposed within the holding reservoir and in fluid communication with the storage reservoir and the output port swells as it fills with the dosage so that the dosage is maintain under pressure. This causes the dosage to discharge to the infusion location.

According to yet another aspect of the invention, the pressurizing components are arranged to maintain the dosage under a pressure that is substantially constant. This is accomplished in one form of the invention by a holding reservoir in the shape of an elongated chamber. The elongated chamber has a substantially constant cross sectional area transverse to a direction of elongation, and as the bladder swells, it is confined to this substantially constant cross sectional shape so that the dosage is maintained at a substantially constant pressure.

Preferably, a capillary element is provided intermediate the holding reservoir and the output port. The capillary element has a microbore that functions to restrict the rate at which the dosage discharges from the bladder.

The above mentioned and other objects and features of this invention and the manner of attaining them will become apparent, and the invention itself will be best understood, by reference to the following description taken in conjunction with the accompanying illustrative drawings.

DESCRIPTION OF THE PREFERRED EMBODIMENTS

Figure 1:
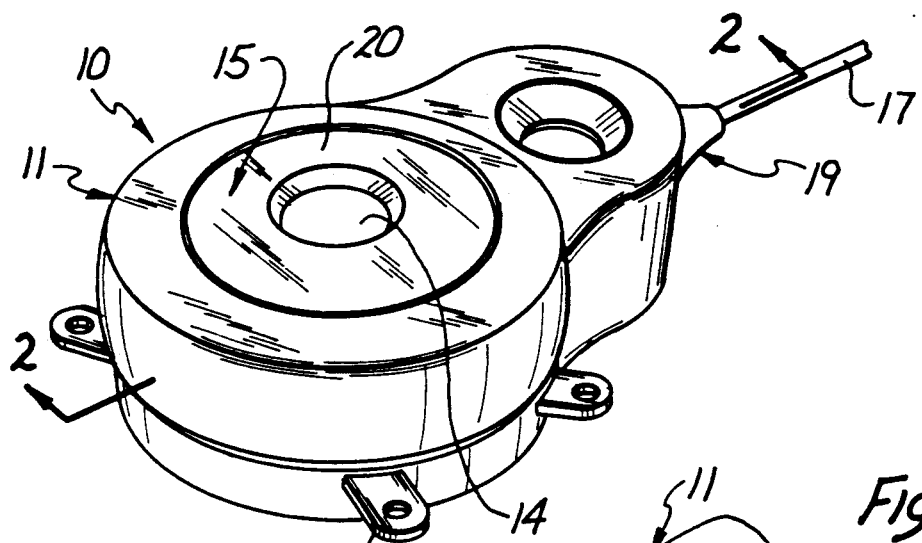
FIG. 1 of the drawings is a perspective view of an implantable infusion system constructed according to the invention.

Referring now to the drawings, there is shown a new and improved infusion system 10 constructed according to the invention. Generally, the system 10 includes an implantable housing 11 (FIGS. 1 and 2) having a storage reservoir 12 (FIG. 2) that is dimensioned and arranged to contain a supply of a medication, and a holding reservoir 13 that is dimensioned and arranged to receive a portion or dosage of the medication from the storage reservoir 12.

Generally, a medication is conventionally injected into the storage reservoir 12 using suitable means such as a hypodermic needle inserted through a self-sealing dome 14 after penetrating the skin. This is usually done after implantation. In order to administer the medication, a dosage of the medication is transferred by a patient-operated pump assembly 15 to the holding reservoir 13 where it is maintained under pressure.

In other words, the patient activates a pump through pump activating components (the combination of these components being termed a "pump assembly 15"). This causes the dosage to be transferred to the holding reservoir 13 from the storage reservoir 12 and ultimately delivered or discharged through an output port 16 and catheter 17 to an infusion location within the body of the patient (not shown), slowly and over a substantially prolonged period of time.

The transferred dosages are multiples of the stroke volume of the delivery pump, a typical stroke volume being between one-tenth and two-tenths cubic centimeters. The holding reservoir is therefore capable of accommodating relatively large doses of drugs. The holding reservoir is designed to maintain or generate a substantially constant pressure level independently from the volume of the drug in the holding reservoir.

Considering the housing 11 in further detail, it is fabricated according to known techniques to have an exterior composed of a biocompatible material such as silicone rubber while interior components may employ a biocompatible thermoplastic composition. A conventional suturing structure 18 at one end (FIGS. 1 and 2) facilitates surgical attachment to the patient, and a catheter connector arrangement 19 at the other end enables attachment of the catheter 17 as part of a conventional implantation procedure.

As an idea of size, the illustrated housing 11 is approximately eight and one-half centimeters long along section line 2—2, six and one-half centimeters wide at its widest point, and three centimeters thick. Of course these dimensions are not critical to the inventive concepts disclosed.

The self-sealing dome 14 employs a known composition of silicone rubber that exhibits the ability to seal itself even after being pierced by a needle repeatedly for inject ion purposes. A medication injected in this way passes to the storage reservoir 12 where it remains until the pump assembly 15 is operated, the volume of the storage reservoir being typically between two and fifty cubic centimeters.

The pump assembly 15 serves as pump means for enabling a patient to cause a dosage of the medication to be transferred from the storage reservoir to the holding réservoir. Reference is made to copending application Ser. No. 195,769, filed May 18, 1988 by Borsanyi et al. for a more detailed description of the pump assembly used in the present device.

Figure 2:
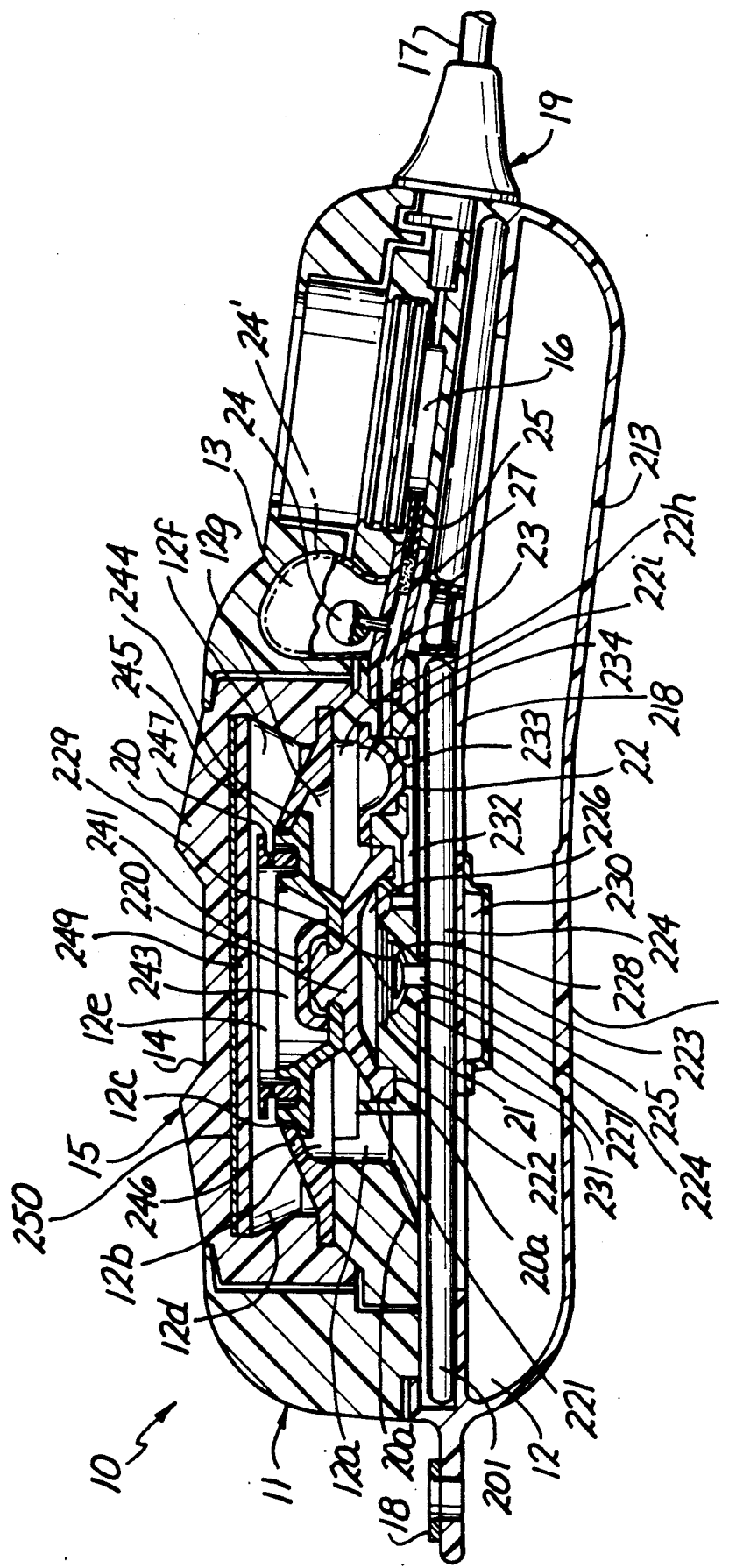
FIG. 2 is an enlarged cross sectional view of the implantable infusion system taken on line 2—2 of FIG. 1.

In order to operate the pump assembly 15, the patient depresses the center or actuator portion 20 of the dome 14 (FIGS. 1 and 2) which is coupled to pump activating components. This causes the pump dome 14 to partially collapse and activate a pump, thereby transferring a quantity of the medication (a single dose) through an inlet valve 21 and an outlet valve 22 to passage 237 and from there to passage 23 that is in fluid communication with a bladder 24 disposed within the holding reservoir 13 (FIG. 2).

The pump is located upon plate 218 and within a separate housing or casing labelled 20, 20a, etc. which can be made in several sections for purpose of manufacture, and which generally surrounds the pump. Specifically, the pump or pump means includes a dome-shaped upper portion 220 formed of silicone rubber or other suitable elastomeric material. The rim 221 of the pump surface is secured within an annular channel 222 provided in the surface of inner wall section 20a of the casing, and a downwardly projecting stem portion 223 of that wall section projects through an opening 224 in the rigid support plate 201. Inlet flow passage 225 extends through the stem portion 223 and places the pump chamber or cavity 26 in communication with the lower chamber 12 of the reservoir.

An annular valve seat 227 is provided at the upper end of passage 225 and is normally engaged by a dish-shaped elastomeric membrane 228 which forms valve member 21 that has its circular outer peripheral portion secured to wall section 20a. Like other components of the device, the membrane 228 of valve member 21 may be formed of silicone rubber. The valve member is provided with openings 229 therethrough that are located outboard of valve seat 227 and that therefore allow flow of fluid between passage 225 and pump chamber 226 only when the valve member membrane 228 is urged away from valve seat 227.

Directly below the pump, and mounted along the underside of the support plate 218, is a rigid filter member in the form of disc 230. The disc may be formed of sintered metal or a fine metallic mesh and is secured in place by an annular rim 231 adhesively bonded to the underside of the support plate 218 about the entrance to inlet passage 225. Directly below the filter disc 30, the surface of the bottom wall of the casing is preferably provided with parallel ribs 213a that prevent the bottom wall from blocking fluid flow from lower chamber 12 into filter 230 and inlet passage 225 should the bottom wall be flexed upwardly into contact with the filter.

A second passage 232 also communicates with the chamber 226 of the pump and leads radially away from the pump through the inner section of the top wall. The second passage 232 is parallel and in close proximity to rigid support plate 218 and communicates at its opposite end with a valve opening 233 defined by an annular flexible lip 234 that is preferably formed integrally with a section of the top wall. The lip defines a valve seat and the opening 233 is normally closed by a cup-shaped elastomeric valve member 22 mounted within cylindrical chamber 236. In its normal, undeformed state, valve member 22 engages lip 234 to maintain the valve in closed condition; however, the valve member is capable of being deformed upwardly into unseated condition to allow fluid flow from second passage 232 and opening 233 into chamber 236 and then into outlet passages 237 and 23. All of the elements described in the above three paragraphs (except when indicated otherwise) are composed of soft, deformable, material such as silicone rubber of the same or differing formulations.

In operation, a syringe is inserted through the indented zone (and septum) 14 of the housing to inject fluid into the fluid reservoir 12. The syringe is inserted until it reaches rigid disk 243, and sufficient medication is injected to fill the storage reservoir 12, as well as fill spaces 225, 245 and 12a through 12h which communicate with each other within the housing.

To use the device, The patient depresses the actuator portion 20 of the dome 14 the number of times necessary to transfer a prescribed dosage of the medication to the holding reservoir 13, each depression or stroke transferring a predetermined quantity.

Depression of portion 20 of the housing, drives septum 14 and rigid disc 243 downwardly, deforming pump portion 220 and substantially exhausting pump cavity 226. Fluid in the pump cavity is driven outward into second passage 232 with the pressure increase beneath outlet valve 22 causing the outlet valve to flex upwardly into open position. An aliquot of fluid substantially equal to the volume of pump chamber or cavity 226 (when the pump housing is undeformed) is therefore discharged to the passage 237 into outlet passage 23. When finger pressure is removed, the top wall returns to its original position largely because of the recovery forces exerted by portion 220 and the flexible top wall portion 20. As the pump cavity 26 expands, the pressure differential causes the membrane valve member 21 to lift away from its seat 227, allowing fluid from the lower reservoir chamber 12 to enter the pump cavity 226 through the first passage 225 and openings 229 in the membrane. Once the pump cavity is filled and pressure is equalized, the inlet valve member 21 closes and the parts again assume the relationships shown in FIG. 2.

The bladder 24 serves as pressurizing means for maintaining the dosage under pressure in the holding reservoir in order to cause the dosage to discharge through the output port. The bladder 24 is composed of an elastomeric material for this purpose, such as a silicone rubber composition, and as it is filled with the dosage, it swells or expands to the position shown in phantom lines in FIGS. 2-4 that is designated with reference numeral 24'.

The hoop stresses created in the inflated elastomeric bladder 24 maintains the dosage under a pressure having a magnitude on the generally order of one to five pounds-per-square-inch, and this causes the dosage to discharge through the output port 16 and the catheter 17 at a more continuous and uniform rate than the pulsed flow from the storage reservoir 12 resulting from operating and discharging the pump directly into the catheter. Hoop stresses are stresses in the elastomeric material resulting from stretching or inflation of the bladder, which tend to force the bladder to return to its original, uninflated state, and thus exert pressure on its contents.

Figure 3:
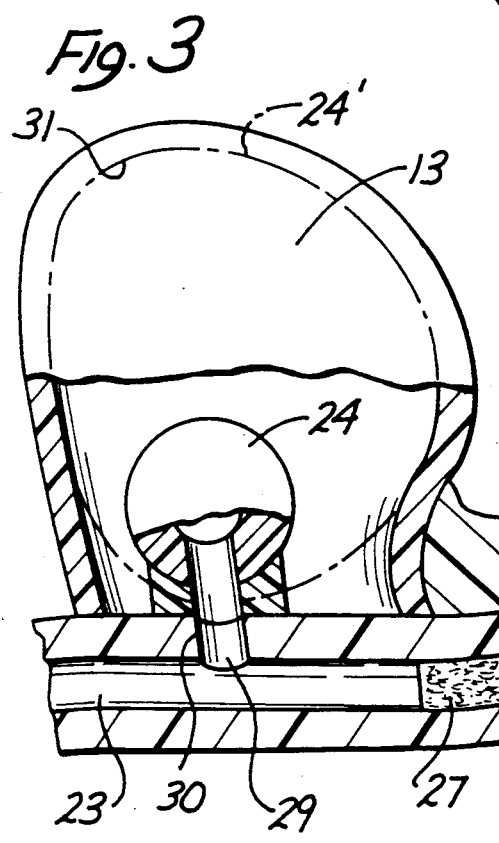
FIG. 3 is a further enlarged cross sectional view of a portion of the housing in which the holding reservoir is located.

To further restrict the flow rate, a capillary element 25 is provided (FIGS. 2 and 3). The capillary element 25 serves as means for restricting the rate at which the dosage discharges from the holding reservoir through the output port. The capillary element 25 is disposed intermediate the holding reservoir 13 and the output port 16 so that the dosage must flow through a microbore 26 in the capillary element 25 (FIG. 2). The capillary element 25 is composed of a suitable material for defining a small precision bore, such as glass or titanium, and the bore 26 it defines has a diameter on the general order of less than one mil (one-tenth mil, for example). This restricts the flow rate from the bladder 24 to the output port 16 as desired, to produce a substantially continuous and constant flow rate over a substantial period of time.

In order to inhibit blockage of the capillary element 25 by particulate material in the dosage, a filter element 27 is provided in a position intermediate the holding reservoir 13 and the capillary element 25. This is composed of a suitable material for this purpose, such as a porous titanium material.

Figure 4:
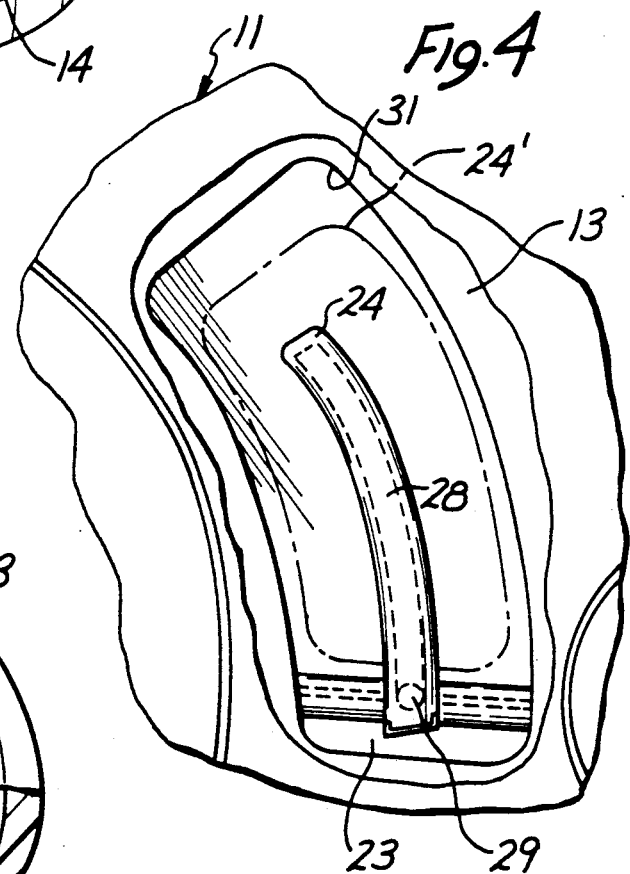
FIG. 4 is an enlarged top view of the portion of the housing in which the holding reservoir is located, with portions broken away to show further details of the holding reservoir.

Further details of the bladder 24 are shown in FIGS. 3 and 4. It includes an elongated body of elastomeric material having a closed hollow interior 2B (FIG. 4) that extends to an opened end 29 (FIG. 3). The opened end 29 is mounted within a hole 30 by suitable means so that the bladder 24 is in fluid communication with the passage 23. Thus, the dosage flows through the passage 23 and the opened end 29 to the interior 2B. As this occurs, the bladder 24 swells, much like a balloon or a section of thin surgical tubing being filled with water.

In other words, the bladder 24 begins swelling at a weaker region of the bladder. It swells until it abuts the reservoir wall 31, and the swelling then continues lengthwise along the bladder 24. The reservoir wall 31 is configured so that the holding reservoir 13 is elongated with a substantially constant cross sectional area transverse to th direction of elongation.

This configuration serves as means for confining the bladder to an elongated shape as the bladder swells, the elongated shape having a substantially constant cross sectional area in a direction transverse to a direction of axial elongation. The hoop stresses increase generally proportionate to the increase in volume of the contents, and therefore maintain the medication at a substantially constant pressure as the volume increases or decreases within the holding reservoir 13. These pressures and the force they create on the medication cause the medication to be discharged over time at a generally constant rate. As a result, the dosage slowly discharges through the capillary element 25.

Figure 5:
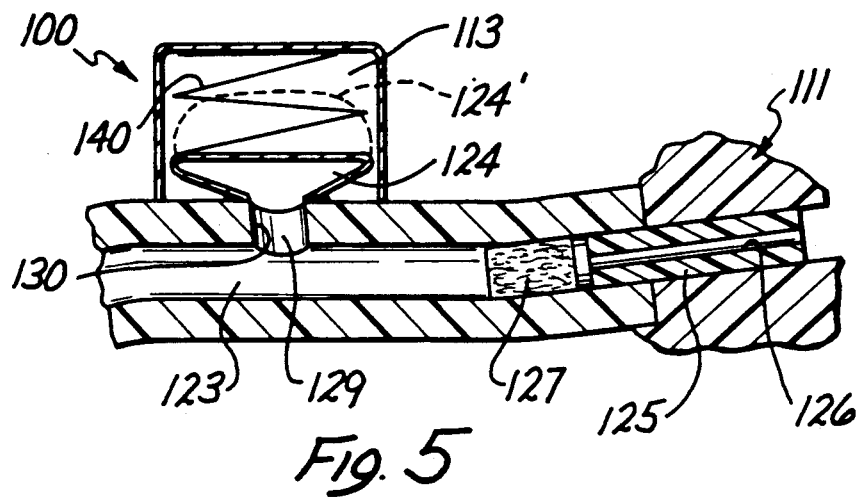
FIG. 5 is an enlarged cross sectional view of a portion of a spring-pressurized holding reservoir.
Figure 6:
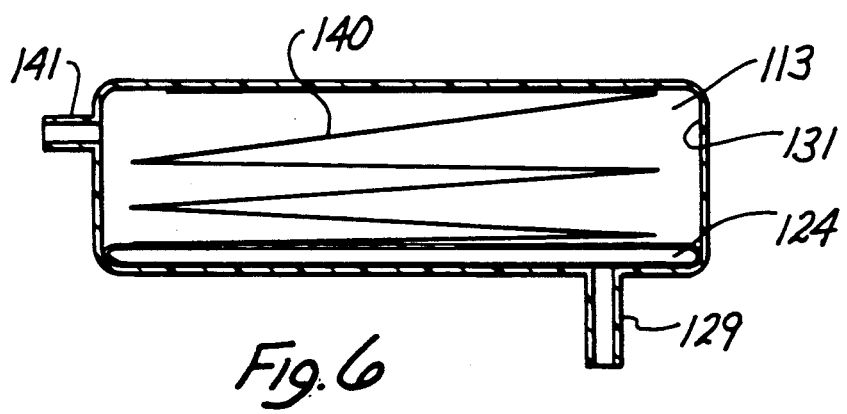
FIGS. 6 and 7 are diagrammatic representations depicting operation of the spring-pressurized holding reservoir.
Figure 7:
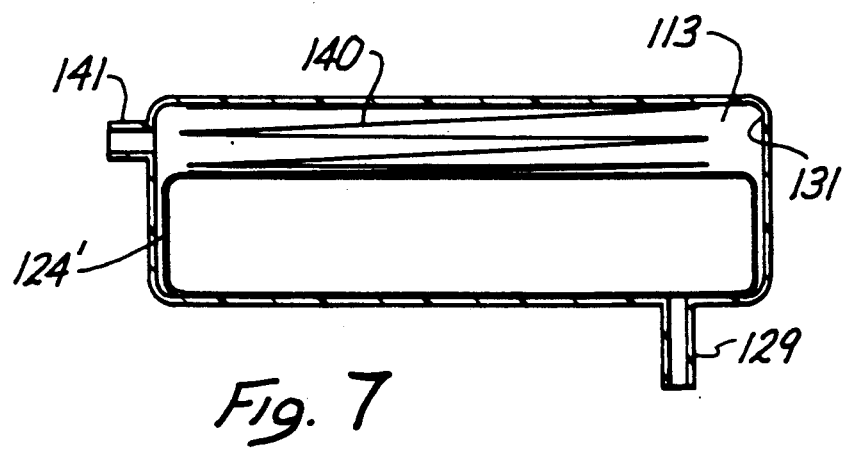

Considering now FIGS. 5–7, there is shown an enlarged cross sectional view of a holding reservoir portion of another embodiment of the invention, a system 100. It is similar in many respects to the system 10, and many reference numerals are increased by one hundred over those designating similar features of the system 10. The similar aspects will not be described in detail.

Like the system 10, the system 100 includes a housing 111 that defines a holding reservoir 113 in which a bladder 124 is disposed so that it can expand within the confines of a reservoir wall 131 from the unexpanded position shown in solid lines in FIG. 5 to the expanded position shown in dashed lines. An opened end 129 of the bladder 124 extends through a hole 130 in the housing so that the bladder is in fluid communication with a passage 123 that extends to a filter element 127 just ahead of a capillary element 125 that defines a microbore 126.

Unlike the system 10, the system 100 includes a spring 140 that is dimensioned and arranged and composed of a suitable material to exert a generally constant force against the bladder 124 and thereby combine with the bladder to serve as pressurizing means for maintaining a dosage under pressure in the holding reservoir in order to cause the dosage to discharge through an output port.

The spring and bladder operate between a substantially empty position, such as that illustrated diagrammatically in FIG. 6, and a substantially full position, such as that illustrated in FIG. 7. A vent 141 relieves pressure on the backside of the bladder 124.

Thus, this invention provides a substantially continuous, constant flow rate that overcomes many problems of the prior art. The dosage is administered a little at a time, over a prolonged period of time. The patient need only stroke the actuator to charge the holding reservoir, with delivery then proceeding slowly, without further patient involvement.

Although an exemplary embodiment of the invention has been shown and described, many changes, modifications, and substitutions may be made by one having ordinary skill in the art without necessarily departing from the spirit and scope of this invention.

What is claimed is:

1. An infusion system comprising a non-metallic housing sized to contain:
    (a) a storage reservoir having inlet means leading from the exterior to the interior of the housing;
    (b) a holding reservoir in fluid communication with the storage reservoir, said holding reservoir being smaller in volume than said storage reservoir;
    (c) an elastomeric bladder means contained within the holding reservoir for maintaining the fluid located therein under continual constant pressure, said bladder means expanding with said fluid to exert said continual constant pressure;
    (d) pump means actuated by external manual pressure for moving a dosage of fluid from the storage reservoir into the holding reservoir, wherein said bladder means expands and exerts said continual constant pressure on said fluid;
    (e) an outlet port leading from the holding reservoir to the exterior of the housing; and
    (f) means for restricting the rate at which fluid discharges from the holding reservoir through the outlet port.

2. The system as recited in claim 1, further comprising:
    catheter means connected in fluid communication with the outlet port for conveying the fluid to a remote location.

3. The infusion system of claim 1 wherein said restricting means includes a capillary element disposed intermediate the holding reservoir and the outlet port.

4. An infusion system comprising a non-metallic housing sized to contain:
    (a) a storage reservoir having inlet means leading from the exterior to the interior of the housing;
    (b) a holding reservoir in fluid communication with the storage reservoir, said holding reservoir being smaller in volume than said storage reservoir;
    (c) an elastomeric wall associated with the holding reservoir for maintaining the fluid located therein under continual constant pressure;
    (d) pump means actuated by external manual pressure for moving a dosage of fluid from the storage reservoir into the holding reservoir, wherein said elastomeric wall expands and exerts said continual constant pressure on said fluid;
    (e) an outlet port leading from the holding reservoir to the exterior of the housing; and
    (f) means for restricting the rate at which fluid discharges from the holding reservoir through the outlet port.

5. The infusion system of claim 4 wherein said restricting means includes a capillary element disposed intermediate the holding reservoir and the outlet port.

6. An infusion system comprising a non-metallic housing sized to contain:
    (a) a storage reservoir having inlet means leading from the exterior to the interior of the housing;
    (b) a holding reservoir in fluid communication with the storage reservoir, said holding reservoir being smaller in volume than said storage reservoir and including at least one elastomeric wall, with the volume of said holding reservoir to the volume of said reservoir being provided to ensure that said elastomeric wall expands upon introduction of said fluid to said holding reservoir to maintain the fluid located therein under continual constant pressure;
    (c) pump means actuated by external manual pressure for moving a dosage of fluid from the storage reservoir into the holding reservoir, wherein said elastomeric wall expands and exerts said continual constant pressure on said fluid;
(d) an outlet port leading from the holding reservoir to the exterior of the housing; and
(e) means for restricting the rate at which fluid discharges from the holding reservoir through the outlet port.

7. The infusion system of claim 6 wherein said restricting means includes a capillary element disposed intermediate the holding reservoir and the outlet port.

* * * * *